(12) United States Patent
Wei et al.

(10) Patent No.: US 11,197,900 B2
(45) Date of Patent: Dec. 14, 2021

(54) LACTIC ACID BACTERIA AND ANTI-INFLAMMATORY METHOD THEREOF

(71) Applicants: Taiwan Enzyme Village Co. Ltd., Chiayi County (TW); National Chiayi University, Chiayi (TW)

(72) Inventors: Chia-Li Wei, Chiayi (TW); Yu-Ting Wang, Chiayi (TW); Tsung-Yi Li, Chiayi (TW); Ya-Chen Huang, Chiayi (TW); Po-Jen Cheng, Chiayi County (TW)

(73) Assignee: TAIWAN ENZYME VILLAGE CO. LTD., Chiayi (TW)

( * ) Notice: Subject to any disclaimer, the term of this patent is extended or adjusted under 35 U.S.C. 154(b) by 67 days.

(21) Appl. No.: 16/402,253

(22) Filed: May 3, 2019

(65) Prior Publication Data

US 2020/0345797 A1    Nov. 5, 2020

(51) Int. Cl.
*A61K 35/747* (2015.01)
*A23L 2/38* (2021.01)

(52) U.S. Cl.
CPC ............ *A61K 35/747* (2013.01); *A23L 2/382* (2013.01)

(58) Field of Classification Search
CPC .............................. A61K 35/747; A23L 2/382
See application file for complete search history.

(56) References Cited

PUBLICATIONS

Entani, E. et al. 1986. *Lactobacillus acetotolerans*, a New Species Fermented from Vinegar Broth. International Journal of Systematic Bacteriology. 36(4): 544-549 (Year: 1986).*
Devi, S. M. et al. 2018. In vitro anti-inflammatory activity among probiotic *Lactobacillus* species isolated from fermented foods. Journal of Functional Foods. 47: 19-27. (Year: 2018).*
Huynh, V. T. et al. 2014. Improved release and metabolism of flavonoids by steered fermentation processes: a review. Int J Mol Sci. 15: 19369-19388. (Year: 2014).*
Swain, M. R. et al. 2014. Fermented Fruits and Vegetables of Asia: A Potential Source of Probiotics. Biotechnology Research International. (Year: 2014).*
Chen, C. L. et al. 2014. Anti-Inflammatory Effects of 81 Chinese Herb Extracts and Their Correlation with the Characteristics of Traditional Chinese Medicine. Evidence-Based Complementary and Alternative Medicine. (Year: 2014).*

* cited by examiner

*Primary Examiner* — Lynn Y Fan
*Assistant Examiner* — Sharon M. Papciak
(74) *Attorney, Agent, or Firm* — Hannah Tien

(57) ABSTRACT

A food composition is disclosed which comprises the acid-resistant bacterial strain *Lactobacillus acetotolerans* LE36. The *L. acetotolerans* LE36 strain has anti-inflammatory properties. The food composition can be further provided as a pharmaceutical composition.

4 Claims, 6 Drawing Sheets

Specification includes a Sequence Listing.

1A

1B

1C

1D

2A

2B

2C

2D

3A

3B

3C

3D
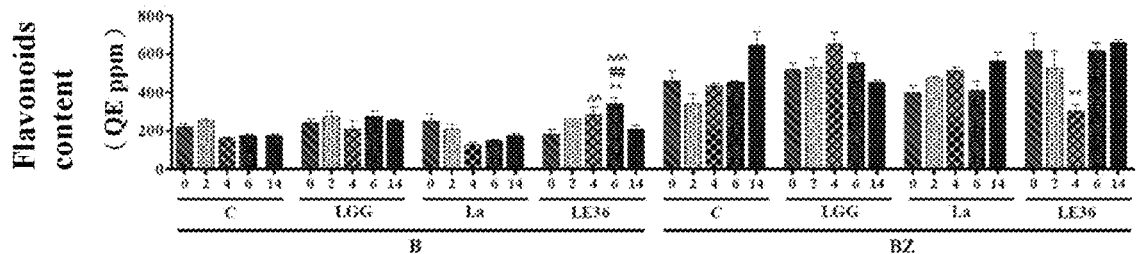
3E
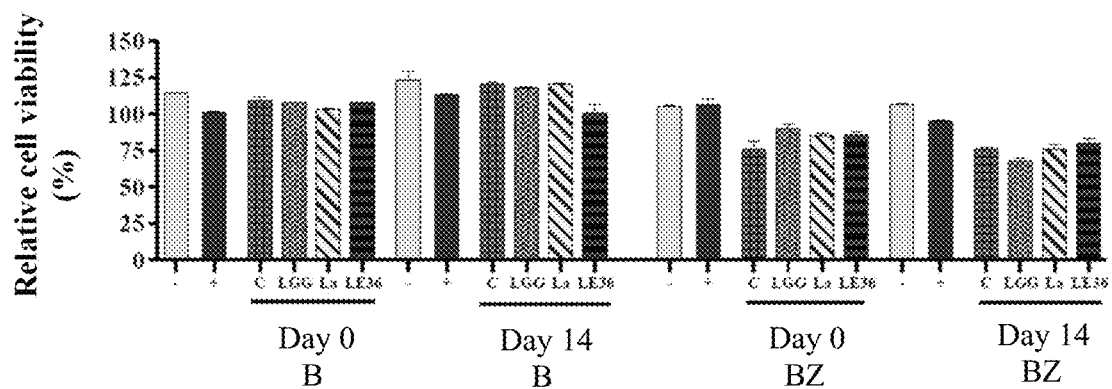
3F
Figure 3
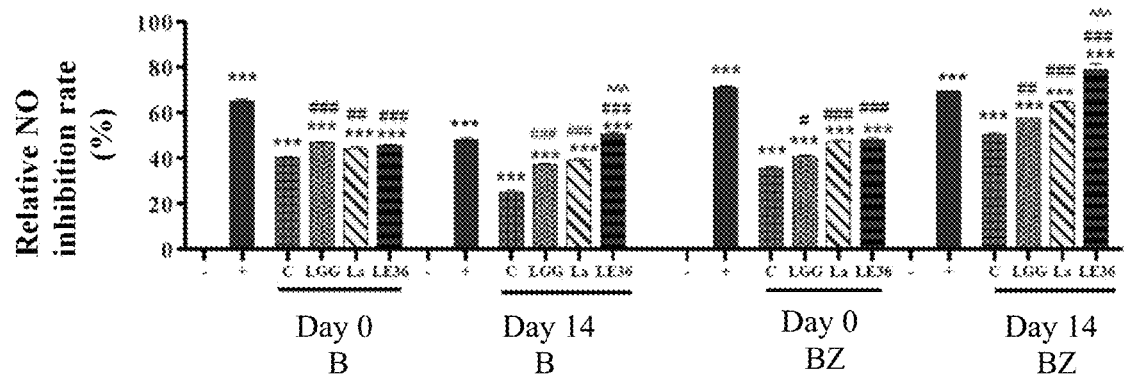

SEQUENCE LISTING

```
<160> NUMBER OF SEQ ID NOS: 1

<210> SEQ ID NO 1
<211> LENGTH: 1522
<212> TYPE: DNA
<213> ORGANISM: Lactobacillus acetotolerans

<400> SEQUENCE: 1
gacgaacgct ggcggcgtgc ctaatacatg caagtcgagc gagccgaact aattgattac      60
cttcgggtat gaagttaggg aagcgagcgg cggatgggtg agtaacacgt gggtaaccta     120
ccctatagtc tgggatacca cttggaaaca ggtgctaata ccggataaaa ggagagatca     180
catgatttct ttttgaaagg cggcgtaagc tgtcgctaaa ggatggaccc gcggtgcatt     240
agctagttgg taaggtaacg gcttaccaag gcaacgatgc atagccgagt tgagagactg     300
atcggccaca ttgggactga gacacggccc aaactcctac gggaggcagc agtagggaat     360
cttccacaat ggacgcaagt ctgatggagc aacgccgcgt gagtgaagaa ggttttcgga     420
tcgtaaagct ctgttgttgg tgaagaaaga tagtgagagt aactgctcat tatttgccgg     480
taatcaacca gaaagtcacg gctaactacg tgccagcagc cgcggtaata cgtaggtggc     540
aagcgttgtc cggatttatt gggcgtaaag cgagcgcagg cggaaagata agtcagatgt     600
gaaagccctc ggcttaaccg aggaatagca tcggaaactg tctttcttga gtgcagaaga     660
ggagagtgga actccatgtg tagcggtgga atgcgtagat atatggaaga acaccagtgg     720
cgaaggcggc tctttggtct gtaactgacg ctgaggctcg aaagcatggg tagcgaacag     780
gattagatac cctggtagtc catgctgtaa acgatgagtg ctaagtgttg ggaggtttcc     840
gcctctcagt gctgcagcta acgcattaag cactccgcct ggggagtacg accgcaaggt     900
taaaactcaa aggaattgac gggggcccgc acaagcggtg gagcatgtgg tttaattcga     960
agcaacgcga agaaccttac caggtcttga catctagtgc caacctaaga gattaggcgt    1020
tcccttcggg gacactaaga caggtggtgc atggctgtcg tcagctcgtg tcgtgagatg    1080
ttgggttaag tcccgcaacg agcgcaaccc ttattattag ttgccagcat taagttgggc    1140
actctaatga gactgccggt gacaaaccgg aggaaggtgg ggatgacgtc aagtcatcat    1200
gccccttatg acctgggcta cacacgtgct acaatgggca gtacaacgag gagcgaactt    1260
```

-continued

```
gtgaaggcaa gcgaatctct gaaagctgtt ctcagttcgg actgtaggct gcaactcgcc      1320
tacacgaagc tggaatcgct agtaatcgcg gatcagcacg ccgcggtgaa tacgttcccg      1380
ggccttgtac acaccgcccg tcacaccatg agagtttgta acacccaaag ccggccggat      1440
aacctagttt actaggagtc agccgtctaa ggtgggacaa atgattaggg tgaagtcgta      1500
acaaggtagc cgtaggagaa cc                                               1522
```

LACTIC ACID BACTERIA AND ANTI-INFLAMMATORY METHOD THEREOF

This application contains a Sequence Listing in computer readable form. The computer readable form is incorporated herein by reference.

FIELD OF THE INVENTION

The present invention provides a lactic acid bacterium which is characterized by having effects of acid-resistance and anti-inflammation.

BACKGROUND OF THE INVENTION

Fermented foods are products of ancient biotechnologies, a critical part of human civilization, and scientific and cultural achievements. Fermented foods are foods made after biochemical and physical changes of raw material caused by microorganisms (such as bacteria, yeasts, fungi, and the likes) or enzymes. The fermentation process can preserve and enhance nutritional values of raw materials of foods, and improve sensory qualities of the foods. Human societies everywhere in the world unexceptionally utilize indigenous sugar sources to prepare fermented beverages.

Fruits and vegetables are rich in antioxidants, including phenolic compounds, carotenoids, anthocyanins, and tocopherols. Most antioxidants are used as reducing agents, metal chelators, singlet oxygen quenchers, and hydrogen donors of polypohenol compounds. Vegetables and fruits are rich in natural phytochemicals having biological activities such as plant growth regulating activity, pigment-providing activity, and anti-viral activity, and these phytochemicals include estrogen and isoflavone of beans, carotenoids of tomatoes and carrots, sulphoraphane of onions and garlic, polyphenols of tea and grapes, or polysaccharides and saponins of Chinese herbal medicines such as ginseng and ganoderma. Others include plant sterols and proteolytic enzyme inhibitors. In addition to be necessary for plant growth and metabolism, these substances can also regulate physiological functions of the human body, such as anti-oxidation, anti-inflammation, anti-allergy, and anti-cancer.

However, the activity of the compounds in vegetables and fruits may be reduced while being stored, prepared or processed. Therefore, in recent years, fermentation methods are used not only to preserve nutritional values of vegetables and fruits during the abundant harvest period and reduce loss of activity, but also to increase the nutritional values by using microbial fermentation. It becomes a very competitive health-care beverage in recent years. Several studies have also shown that lactic acid bacteria fermentation improves the antioxidant capacity of vegetables and fruits, such as ascorbic acid, glutathione and phenolic compounds. The enhancement of antioxidant capacity during fermentation is mainly attributed to biologically active compounds released by lactic acid bacteria. In addition, studies have shown that through the fermentation process, the conjugated form of the phenolic compounds can be biotransformed into a free form, thereby improving their health-related functions.

Lactic acid bacteria have been used in foods to produce inhibitory peptides of angiotensin converting-enzyme and gamma-aminobutyric acid (GABA) for preventing and treating hypertension. In general, antioxidants are capable of preventing automatic oxidation of food ingredients and therefore suitable for being used in manufacturing processes and finished products of food and beverage. For the aforementioned reasons, fermentation of food materials is a useful tool for improving the antioxidant activity of food products. Therefore, lactic acid bacteria fermentation is a potential alternative to expanding the usage of processed foods.

In addition, in recent years, Chinese herbal medicines have received more and more attentions as a medicine. It is mainly because of the relatively low cost of Chinese herbal extracts, and almost no toxicities or side effects has ever been found clinically. As a result, Chinese herbal medicines have been used as alternative medicines in China, Japan, Korea and other countries to treat a variety of human diseases including cancer. A combination of Chinese herbal medicines is used in Asian countries as a formula capable of enhancing therapeutic effects and reducing adverse reactions. For example, Radix Polygalae is the root of *Polygala tenuifolia* willd. or *Polygala sibirica* L., perennial herb of Polygalaceae, widely distributed in different regions in Asia, such as China and South Korea. It is a famous traditional medicine having the effects of discharging phlegm, relieving swelling, reinforcing deficiency, soothing, antidepressants, and antipsychotics. It is more commonly used in neurotherapy, for example, memory loss, neurasthenia, palpitations, and insomnia. The main components of Radix *Polygala* include tenuigenin (a triterpenoid saponin), polygalasaponin (a triterpenoid saponin), polygalitol, xanthone, and oligosaccharides. Studies show that dozens of flavonoids isolated from Radix *Polygala* have antioxidant activity and inhibit the production of nitric oxide (NO) in BV-2 microglial cells stimulating with lipopolysaccharide (LPS).

Therefore, vegetables and fruits are the main source of many nutrients, but it is possible that the nutrients might be lost while being stored, prepared or processed. Inoculation of probiotics is a method commonly used to maintain the nutritional values of vegetables and fruits and to increase their biological activity.

SUMMARY OF THE INVENTION

The present invention relates to a *Lactobacillus acetotolerans* LE36, which has an anti-inflammatory function. In addition, the *Lactobacillus acetotolerans* LE36 can be further provided as a food composition or a pharmaceutical composition. At the same time, the *Lactobacillus acetotolerans* LE36 can be further used in anti-inflammatory methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIGS. 1A, 1C and 1E) or at 42° C. (FIGS. 1B, 1D and 1F) for 144 or 96 hours, and samples are collected and OD600 is measured at the 0th, 12th, 18th, 24th, 48th, 72nd, 96th and 144th hour.

(FIG. 2D) *$p<0.05$ and ***$p<0.001$ are the "+" and each re-fermentation juice groups versus the "−" group; ####$p<0.001$ is each re-fermentation juice after inoculation versus the respective juice before inoculation ("b" group); ^$p<0.05$, ^^$p<0.01$ and ^^^$p<0.001$ are each re-fermentation juice after inoculation for 2-4 days versus the respective juice after inoculation for 0 day.

(FIGS. 3C-3D) *$p<0.05$, $p<0.01$ and *$p<0.001$ are each re-fermentation juice after 2-14 days of inoculation versus the respective juice after 0 day of inoculation; #$p<0.05$, ##$p<0.01$ and ###$p<0.001$ are each re-fermentation juice after inoculation of lactic acid bacteria versus the respective juice without inoculation of any bacteria (the control group "C") after same days of incubation; ^^$p<0.01$ and ^^^$p<0.001$ are re-fermentation juice inoculated with LE36 versus the respective juice inoculated with La after same days of incubation. (FIG. 3F) ***$p<0.001$ is the "+" and each re-fermentation juice groups versus the "−" group; #$p<0.05$, ##$p<0.01$, and ###$p<0.001$ are the re-fermentation juices after inoculation of yeast versus the respective juice without inoculation of any yeast (the control group "C") after same days of incubation; ^^^$p<0.001$ is re-fermentation juice inoculated with LE36 versus the respective juice inoculated with La after same days of incubation.

DETAILED DESCRIPTION OF THE INVENTION

Figure 1:
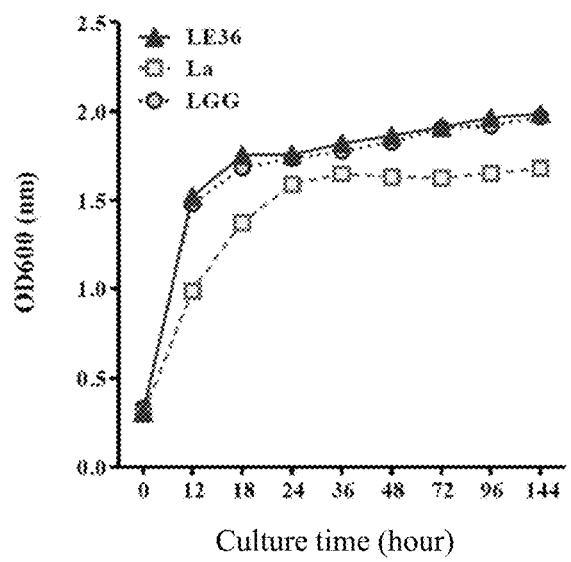
FIG. 1 shows the growth curves of *Lactobacillus acetotolerans* LE36 cultured at different temperatures and pH values. The bacterial culture of the *Lactobacillus acetotolerans* isolate LE36 (LE36), and the control groups of *Lactobacillus acetotolerans* type strain (La) and the *Lactobacillus rhamnosus* GG (LGG) at $OD600=0.02$ are respectively inoculated in MRS broth at pH 5.4 (FIGS. 1A and 1B), 4.8 (FIGS. 1C and 1D), and 4.2 (FIGS. 1E and 1F), and respectively cultured at 37° C.
Figure 1:
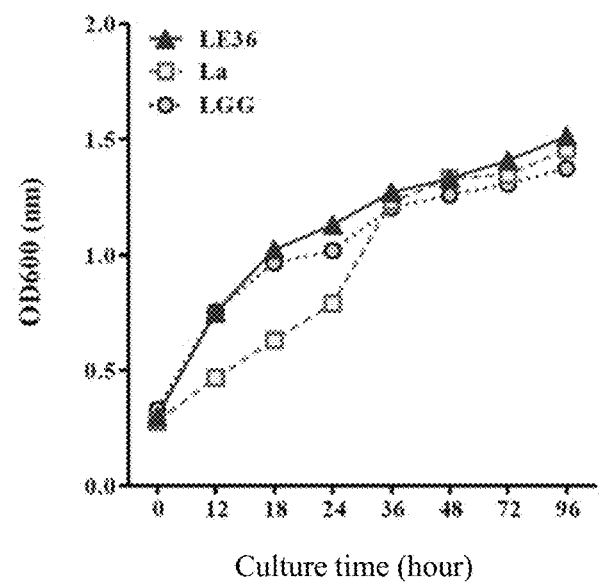
Figure 1:
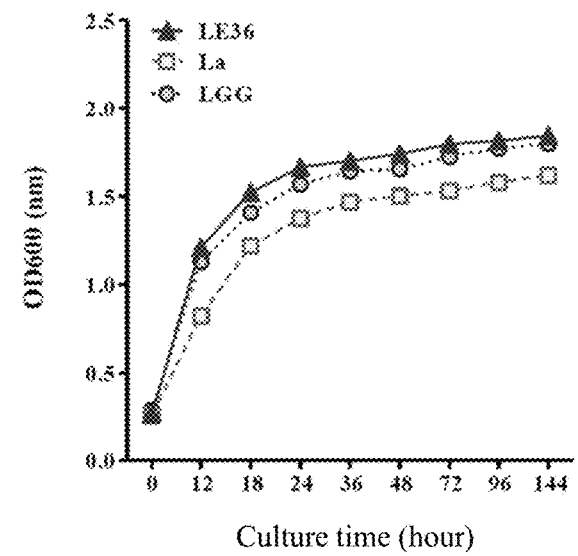
Figure 1:
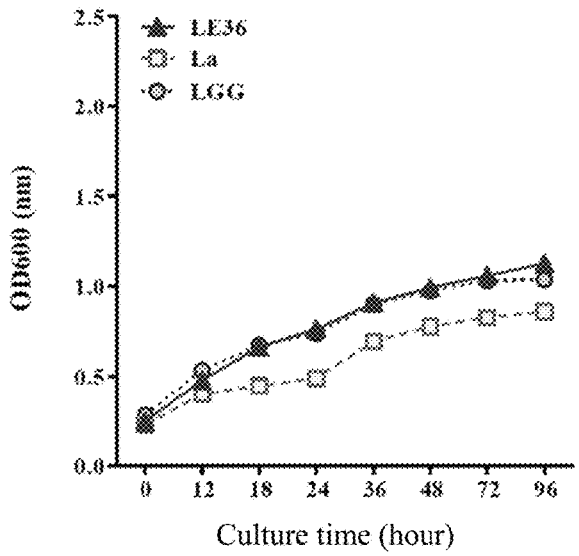
Figure 1:
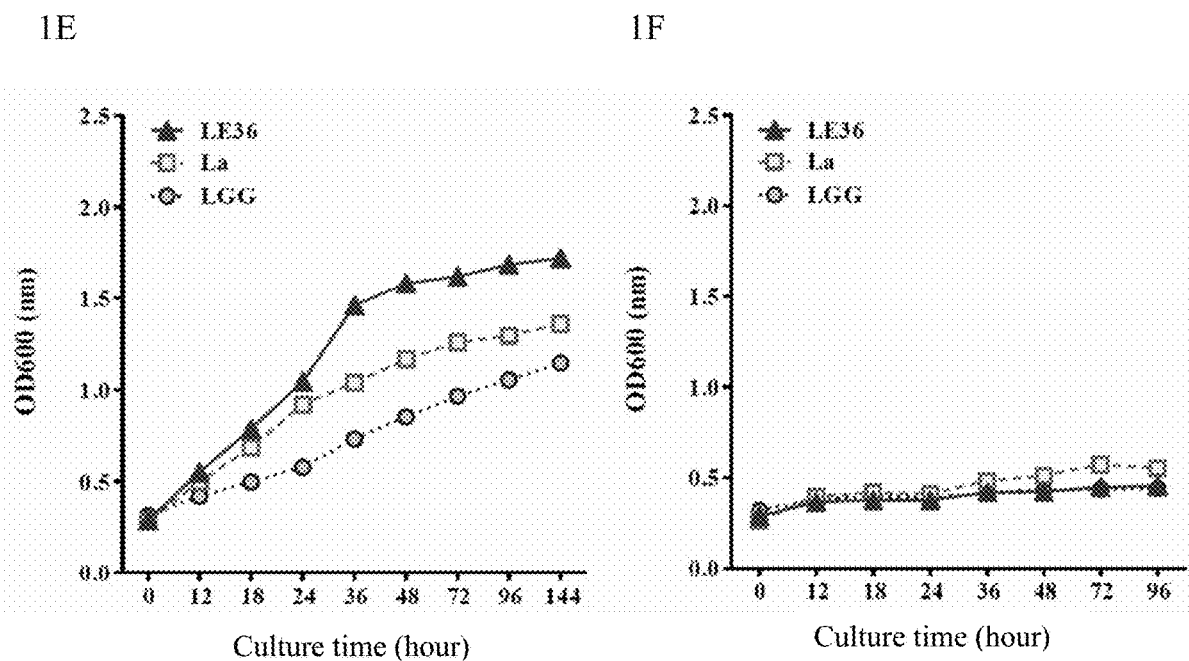

Inoculation of probiotics is a common approach of maintaining nutritional values and enhancing biological activities of vegetables and fruits. In order to enhance the biological activities of vegetable and fruit fermentation juice and promote market competitiveness of their products, the present invention firstly obtains *Lactobacillus acetotolerans* LE36 from aging broths of fruit and vegetable fermentation juices in Taiwan Enzyme Village Co., Ltd., by plating on MRS agars containing $NaN_3$ and cycloheximide following anaerobic incubation at pH 4.8, Gram stain test, inoculation in pineapple or papaya fermentation juice supplemented without or with Radix *Polygala* at 30° C. incubation, 16S rDNA sequencing, physiological and biochemical analyses. In an acid resistance test using acetic acid for pH adjustment, the bacteria count of LE36 (OD600 is 1.46 and 1.72) cultured in the MRS broth at pH 4.2 for 36 and 144 hours at 37° C. is significantly better than that of the *Lactobacillus rhamnosus* GG (LGG) (OD600 is 0.73 and 1.15) and *Lactobacillus acetotolerans* type strain (La; OD600 is 1.04 and 1.35). Subsequently, LE36 is inoculated in 5 fermentation juice supplemented with Radix *Polygala* for 4 days, the viable bacteria count of the LE36 can be maintained in all fermentation juice. As to the anti-inflammation effect of the heat-treated supernatant sample of the re-fermentation juice in the LPS-stimulated RAW264.7 cells, when the inoculated re-fermentation juice is compared to the re-fermentation juice before being inoculated, the Radix *Polygala*-added bean sprouts fermentation juice (BZ) has an significant increase of 181%. After being incubated for 4 days, the NO inhibition rate of the Radix *Polygala*-added pineapple, papaya and bean sprouts fermentation juice (AZ, PZ, and BZ) increase significantly by 53%, 19% and 46%, respectively.

In the present invention, LE36, LGG and La are further inoculated respectively in the bean sprouts fermentation juice with or without Radix *Polygala*. In the resulted re-fermentation juice B and BZ, only the one inoculated with LE36 shows the fermenting effect of continuously increasing the number of viable lactic acid bacteria ($1.6 \times 10^8$ and $2.5 \times 10^8$ CFU/mL respectively after 14 days of fermentation), and continuously consuming reducing sugar content (reduction by 56% and 52%, respectively, after 14 days of fermentation). As to the flavonoids content, only the re-fermentation juice B inoculated with LE36 shows a significant improvement effect (51.6%) after 6 days of fermentation. Finally, in the anti-inflammation test for inhibiting NO production, the re-fermentation juice B and BZ inoculated with LE36 for 14 days increase respectively by 100% and 30% as compared to those without inoculation, and increase respectively by 56% and 22% as compared to those inoculated with La.

Therefore, the *Lactobacillus acetotolerans* LE36 selected from the present invention is more resistant to acid than the same species, is more suitable for being used in a vegetable and fruit fermentation juice having a pH of 3 to 4, and can increase the number of viable lactic acid bacteria and anti-inflammatory activity, and can be applied to the development of functional beverages in the future.

The term "a" or "an" as used herein is to describe elements and ingredients of the present invention. The term is only used for the convenience of description and for provision of the fundamental concepts of the present invention. The description should be understood as comprising one or at least one, and unless otherwise explicitly indicated by the context, singular terms include pluralities and plural terms include the singular. When used in conjunction with the word "comprising" in a claim, the term "a" or "an" may mean one or more than one.

The term "or" as used herein refers to "and/or."

The present invention provides an isolated *Lactobacillus acetotolerans* LE36 deposited under DSMZ Accession No. DSM 33168.

In one embodiment, the acid resistance of the *Lactobacillus acetotolerans* LE36 ranges from pH 1 to pH 6. In a preferred embodiment, the acid resistance of the *Lactobacillus acetotolerans* LE36 ranges from pH 2 to pH 5. In a more preferred embodiment, the acid resistant of the *Lactobacillus acetotolerans* LE36 ranges from pH 3 to pH 4.

In another embodiment, the *Lactobacillus acetotolerans* LE36 has a function of facilitating flavonoid production.

In one embodiment, the *Lactobacillus acetotolerans* LE36 has an anti-inflammatory function.

The present invention also provides a composition, which comprises a *Lactobacillus acetotolerans* LE36 deposited under DSMZ Accession No. DSM 33168.

In one embodiment, the acid resistance of the *Lactobacillus acetotolerans* LE36 ranges from pH 1 to pH 6. In a preferred embodiment, the acid resistance of the *Lactobacillus acetotolerans* LE36 ranges from pH 2 to pH 5. In a more preferred embodiment, the acid resistant of the *Lactobacillus acetotolerans* LE36 ranges from pH 3 to pH 4.

In another embodiment, the composition is a medicine, feed, a beverage, a nutritional supplement, a dairy product, a food product, a healthy food or a health-care food. In a preferred embodiment, the food product is a fermented food product. In a more preferred embodiment, the fermented food is a fermentation juice.

In one embodiment, the fermentation juice comprises a vegetable and fruit fermentation juice. In a preferred embodiment, the fermentation juice comprises an acidic vegetable and fruit fermentation juice.

In another embodiment, the composition further comprises a Chinese herbal medicine or an extract thereof. In a preferred embodiment, the Chinese herbal medicine comprises Radix Polygalae.

In one embodiment, the composition further comprises an additive selected from the group consisting of an excipient, a preservative, a diluent, a filler, an absorption enhancer, a sweetener, and a combination thereof.

In another embodiment, the dosage form of the composition is a powder, a tablet, a granulation, a suppository, a microcapsule, an ampoule, a liquid spray, or a suppositorium.

In a preferred embodiment, the *Lactobacillus acetotolerans* LE36 has a function of facilitating flavonoids production.

In another embodiment, the composition has an anti-inflammatory function. In a preferred embodiment, the *Lactobacillus acetotolerans* LE36 has an anti-inflammatory function.

In one embodiment, the composition is a food composition or a pharmaceutical composition.

The present invention further provides a food composition, which comprises a *Lactobacillus acetotolerans* LE36 deposited under DSMZ Accession No. DSM 33168.

In one embodiment, the acid resistance of the *Lactobacillus acetotolerans* LE36 ranges from pH 1 to pH 6. In a preferred embodiment, the acid resistance of the *Lactobacillus acetotolerans* LE36 ranges from pH 2 to pH 5. In a more preferred embodiment, the acid resistant of the *Lactobacillus acetotolerans* LE36 ranges from pH 3 to pH 4.

In an embodiment of the food composition, it can be a food product in combination with a physiologically acceptable excipient or diluent. In one embodiment, the food composition comprises a fermented food composition. As used herein, the "fermented food composition" refers to a type of food product processed and prepared by using beneficial microorganisms, such as yogurt, cheese, fermented glutinous rice, pickles, soy sauce, edible vinegar, fermented soybeans, yellow rice wine, beer, wine, and vegetable and fruit fermentation juice. In a preferred embodiment, the fermented food composition comprises a fermentation juice. In a more preferred embodiment, the fermentation juice comprises a vegetable and fruit fermentation juice.

In another embodiment, the vegetable and fruit fermentation juice comprises a pineapple fermentation juice, a papaya fermentation juice, a bean sprouts fermentation juice, a jaboticaba fermentation juice, and a grapefruit/pumpkin/tangerine fermentation juice. In a preferred embodiment, the vegetable and fruit fermentation juice comprises a pineapple fermentation juice, a papaya fermentation juice and a bean sprouts fermentation juice. In a more preferred embodiment, the vegetable and fruit fermentation juice comprises a bean sprouts fermentation juice.

In one embodiment, the food composition further comprises a Chinese herbal medicine or an extract thereof. In a preferred embodiment, the Chinese herbal medicine comprises Radix Polygalae.

In one embodiment, the *Lactobacillus acetotolerans* LE36 has a function of facilitating the production of flavonoids in the food composition. In a preferred embodiment, the *Lactobacillus acetotolerans* LE36 has a function of facilitating the production of flavonoids in the fermented food composition. In a more preferred embodiment, the *Lactobacillus acetotolerans* LE36 has a function of facilitating the production of flavonoids in the vegetable and fruit fermentation juice.

In another embodiment, the *Lactobacillus acetotolerans* LE36 has a function of enhancing anti-inflammatory function in the food composition. In a preferred embodiment, the *Lactobacillus acetotolerans* LE36 has a function of enhancing the anti-inflammatory function in the fermented food composition. In a more preferred embodiment, the *Lactobacillus acetotolerans* LE36 has a function of enhancing the anti-inflammatory function in the vegetable and fruit fermentation juice.

As used herein, "anti-inflammation" refers to alleviating an inflammatory response, specifically, reducing one or more indicators of an inflammatory response, such as reducing the level of cytokines or mediators in serum that cause or potentiate an inflammatory response, and reducing the secretion of hormones or mediators from inflammation-related cells. In a preferred embodiment, the anti-inflammation comprises reducing NO production.

In one embodiment, the fermentation juice comprises an acidic fermentation juice. In a preferred embodiment, the fermentation juice comprises an acidic vegetable and fruit fermentation juice. The term "acidic" as used herein refers to a pH value of 1-6, preferably a pH value of 2-5, and a more preferred pH value of 3-4.

In another embodiment, the form of the food composition is a food product, a healthy food product, or a health-care food product.

The present invention also provides a food composition, which comprises an acid-resistant lactic acid bacteria strain and a vegetable and fruit fermentation juice, wherein the acid-resistant lactic acid bacteria strain is a *Lactobacillus acetotolerans* LE36 deposited under DSMZ Accession No. DSM 33168.

In one embodiment, the vegetable and fruit fermentation juice comprises a pineapple fermentation juice, a papaya fermentation juice, a bean sprouts fermentation juice, a jaboticaba fermentation juice, and a grapefruit/pumpkin/tangerine fermentation juice. In a preferred embodiment, the vegetable and fruit fermentation juice comprises a pineapple fermentation juice, a papaya fermentation juice, and a bean sprouts fermentation juice. In a more preferred embodiment, the vegetable and fruit fermentation juice comprises a bean sprouts fermentation juice.

The present invention also provides a food composition, which comprises an acid-resistant lactic acid bacteria strain and an acidic fermentation juice, wherein the acid-resistant lactic acid bacteria strain is a *Lactobacillus acetotolerans* LE36 deposited under DSMZ Accession No. DSM 33168.

In one embodiment, the pH value of the acidic fermentation juice ranges from 1 to 6. In a preferred embodiment, the pH value of the acidic fermentation juice ranges from 2 to 5. In a more preferred embodiment, the pH value of the acidic fermentation juice ranges from 3 to 4. In another embodiment, the acidic fermentation juice comprises an acidic vegetable and fruit fermentation juice. In a preferred embodiment, the acidic vegetable and fruit fermentation juice comprises a pineapple fermentation juice, a papaya fermentation juice, and a bean sprouts fermentation juice. In a more preferred embodiment, the acidic vegetable and fruit fermentation juice comprises a bean sprouts fermentation juice.

In another embodiment, the food composition further comprises a Chinese herbal medicine or an extract thereof. In a preferred embodiment, the Chinese herbal medicine comprises Radix Polygalae.

The present invention further provides a pharmaceutical composition comprising an acid-resistant lactic acid bacteria strain, which comprises a *Lactobacillus acetotolerans* LE36 deposited under DSMZ Accession No. DSM 33168.

In one embodiment, the pH value of the acid resistance of the *Lactobacillus acetotolerans* LE36 ranges from 1 to 6. In a preferred embodiment, the pH value of the acid resistance of the *Lactobacillus acetotolerans* LE36 ranges from 2 to 6. In a more preferred embodiment, the pH value of the acid resistance of the *Lactobacillus acetotolerans* LE36 ranges from 3 to 4.

In another embodiment, the pharmaceutical composition has an anti-inflammatory function. In a preferred embodiment, the *Lactobacillus acetotolerans* LE36 has an anti-inflammatory function.

In one embodiment, the pharmaceutical composition further comprises a Chinese herbal medicine or an extract thereof. In a preferred embodiment, the Chinese herbal medicine comprises Radix Polygalae.

In another embodiment, the pharmaceutical composition further comprises a pharmaceutically acceptable salt or solvate, and a pharmaceutically acceptable carrier and/or excipient.

The pharmaceutical compositions of the present invention can be administered topically or systemically by any methods known in the art, including, but not limited to, by intramuscular, intradermal, intravenous, subcutaneous, intraperitoneal, intranasal, oral, mucosal administration or external routes. Suitable routes of administration, methods of formulation, and schedule of administration can be determined by those who skilled in the art. In the present invention, the pharmaceutical composition can be formulated in various forms according to corresponding administration routes, such as a liquid solution, a suspension, an emulsion, a syrup, a tablet, a pill, a capsule, a sustained release formulation, powders, granules, an ampoule, an injection solution, an infusion solution, a kit, an ointment, a lotion, a liniment, a cream, or a combination thereof. When necessary, it can be sterilized or mixed with any pharmaceutically acceptable carriers and/or excipients.

In the present invention, the term "carrier" or "excipient" refers to any substance that is not itself a therapeutic agent, but is used as a carrier and/or a diluent and/or an adjuvant or a vehicle for delivering a therapeutic agent to an individual, or is added to a formulation to improve the handling or storage properties of the formulation, or to allow or facilitate the dosage unit of the composition to form a dosage unit (such as a capsule or a tablet) suitable for oral administration. Suitable carriers or excipients are well known to those of ordinary skill in the art of preparing pharmaceutical formulations or food products. The carriers or excipients may include, by way of example and not limitation, a buffer, a diluent, a disintegrating agent, a binder, an adhesive, a wetting agent, a polymer, a lubricant, a slip agent, a substance added to mask or counteract undesirable tastes or flavors, a flavoring agent, a pigment, an aromatic agent, and a substance added to improve the appearance of the composition. Acceptable carriers or excipients include a citrate buffer, a phosphate buffer, an acetate buffers, a bicarbonate buffer, stearic acid, magnesium stearate, magnesium oxide, a sodium salt and calcium salt of phosphoric acid and sulfuric acid, magnesium carbonate, talc, gelatin, arabic gum, sodium alginate, pectin, dextrin, mannitol, sorbitol, lactose, sucrose, starch, gelatin, a cellulosic material (such as a cellulose ester of alkanoic acid and a cellulose alkyl ester), a low melting point wax, cocoa butter, an amino acid, urea, alcohols, ascorbic acid, a phospholipid, a protein (e.g. serum albumin), ethylenediaminetetraacetic acid (EDTA), dimethyl sulfoxide (DMSO), sodium chloride or other salts, a liposome, mannitol, sorbitol, glycerol or powders, a polymer (such as polyvinyl pyrrolidone, polyvinyl alcohol and polyethylene glycol), and other pharmaceutically acceptable substances. The carrier should not destroy the pharmacological activity of a therapeutic agent and should be non-toxic when administered at a dose sufficient to deliver a therapeutic amount of therapeutic agent.

In another embodiment, the pharmaceutical composition comprises an oral dosage form or an external dosage form; the oral dosage form is, for example, a tablet, a capsule, a solution, powders, and the likes. The external dosage form is, for example, a cream, a spray, a gel, powders or a cream.

The present invention further provides a use of an acid-resistant lactic acid bacteria strain for preparing an anti-inflammatory composition, wherein the acid-resistant lactic acid bacteria strain is a *Lactobacillus acetotolerans* LE36 deposited under DSMZ Accession No. DSM 33168.

In one embodiment, the pH value of the acid resistance of the *Lactobacillus acetotolerans* LE36 ranges from 1 to 6. In a preferred embodiment, the pH value of the acid resistance of the *Lactobacillus acetotolerans* LE36 ranges from 2 to 5. In a more preferred embodiment, the pH value of the acid resistance of the *Lactobacillus acetotolerans* LE36 ranges from 3 to 4.

In another embodiment, the *Lactobacillus acetotolerans* LE36 has a function of facilitating flavonoids production.

In one embodiment, the *Lactobacillus acetotolerans* LE36 has an anti-inflammatory function.

In another embodiment, the composition further comprises a Chinese herbal medicine or an extract thereof. In a preferred embodiment, the Chinese herbal medicine comprises Radix Polygalae.

In other embodiments of the present invention, the composition is a pharmaceutical composition. In a preferred embodiment, the pharmaceutical composition further comprises a pharmaceutically acceptable salt or solvate, and a pharmaceutically acceptable carrier and/or excipient.

In still other embodiments of the present invention, the composition is a food composition. In a preferred embodiment, the form of the food composition is a food product, a healthy food product or a health-care food product.

In another embodiment, the food composition comprises a fermented food composition. In a preferred embodiment, the fermented food composition comprises a fermentation juice. In a more preferred embodiment, the fermentation juice comprises a vegetable and fruit fermentation juice.

In one embodiment, the fermentation juice comprises an acidic fermentation juice. In a preferred embodiment, the fermentation juice comprises an acidic vegetable and fruit fermentation juice.

The present invention further provides an anti-inflammatory method, which comprises administering to a subject suffering from an inflammatory condition a composition, wherein the composition comprises an effective amount of *Lactobacillus acetotolerans* LE36 deposited under DSMZ Accession No. DSM 33168.

The composition is capable of treating the inflammatory condition of the subject. The term "treating" as used herein includes reducing the severity of inflammation, delaying the onset of inflammation, relieving inflammation, alleviating symptoms caused by inflammation, or stopping the symptoms caused by inflammation. The term "treating" includes, but is not limited to, prophylactic and/or therapeutic treatment.

The term "effective amount" as used herein is a therapeutic amount that prevents, reduces, stops, or reverses the development of a symptom of a subject under specific conditions, or partially, completely alleviates the subject from a symptom that already exists under specific conditions when the treatment begins.

In one embodiment, the subject is an animal, preferably a mammal, and more preferably a human.

In another embodiment, the composition is a pharmaceutical composition. The pharmaceutical composition can further comprise a pharmaceutically acceptable carrier, which can be administered to a subject via a number of different routes of commonly known treatment methods in the field related to the present invention.

In some embodiments, the composition and the pharmaceutically acceptable carrier are administered via external, intravenous, intramuscular, subcutaneous, topical, oral, or inhalation administration. The composition will be delivered to a target site through the digestive and circulatory system. In a preferred embodiment, the drug is administered via an oral route.

Therefore, it is a trend to add lactic acid bacteria into fermented food products, and uses of fermentation juice can promote body health. The present invention thus adds the selected *Lactobacillus acetotolerans* LE36 and the traditional Chinese medicine Radix Polygalae to enhance the anti-inflammatory activity of fermentation juice. It can be learned from the present invention that after fermentation juice are inoculated with LE36 and fermented for 14 days, regardless of the addition of Radix Polygalae, as compared to other two added lactic acid bacteria, the anti-inflammatory effect of all fermentation juice is improved. Accordingly, the present invention can confirm that the addition of the *Lactobacillus acetotolerans* LE36 into vegetable and fruit fermentation juice for re-fermentation, and after a long period of fermentation, the lactic acid strains can continue to grow, and have an anti-inflammatory effect.

According to the present invention, the *Lactobacillus acetotolerans* LE36 can be included in a pharmaceutical composition, a dietary supplement, a food product, a healthy food, a therapeutic food or a component thereof, which are generally consumed by a human. The *Lactobacillus acetotolerans* LE36 of the present invention can be delivered in the form of a food product.

EXAMPLES

The embodiment of the present invention could be implemented with different content and is not limited to the examples described in the following text. The following examples are merely representative of various aspects and features of the present invention.

Experimental Method (1) Preparation of Lactic Acid Bacteria

The preparation steps of the lactic acid bacteria are as follows:

(a) Activation of lactic acid bacteria: the lactic acid bacteria were removed from the cryopreservation tube and streaked on a MRS agar plate and cultured at 37° C. for two days, so these were colonies of the bacterial strains activated one time. Ten colonies were selected and restreaked on the MRS agar plate, after being cultured in the same manner (colonies of bacterial strain activated twice), stored at 4° C., and the colonies were activated once every 2 weeks.

(b) Preparation of lactic acid bacterial culture: 5 to 10 colonies, selected from the colonies of bacterial strains activated at least twice, were inoculated into a 15 mL centrifuge tube containing 5 mL of MRS broth, and cultured in an incubator at 37° C. for 24 hours (which was the one-time activated bacterial culture).

(c) Preparation of lactic acid bacteria cryotube: 5 mL of one-time activated bacterial culture was centrifuged at 5000 g for 15 minutes at room temperature, and then resuspended in a concentrated NB broth/10% dimethyl sulfoxide (DMSO). 1 mL of bacterial solution was aliquoted and stored at −80° C.

(d) Lactic acid bacteria plating and counting: samples of the lactic acid bacterial culture, aging broth of fruit and vegetable fermentation juice, re-fermentation juice, etc., were diluted 10 folds successively with phosphate buffered saline (PBS) in laminar flow. 100 μL of the sample dilution was placed in MRS or MRS/sodium azide (NaN$_3$)/cycloheximide agar plates, spread evenly using 3 mm sterile glass beads, and cultured at 37° C. for 4 to 6 days.

(e) Lactic acid bacteria identified by Gram staining method: sterile water was dropped on a clean slide glass, colonies on the agar plate were picked up and evenly spread on the slide glass, passed the flame 2-3 times, fixed and then stained with a Gram staining kit. The slide glass first was stained with crystal violet for 1 minute, then the pigment was washed off with water, and fixed with several drops of Gram's iodine. After 1 minute, the slide glass was rinsed with 95% ethanol, decolorized, and finally re-stained with Hucker's safranin for 45 seconds, and then the pigment was washed off with water. The slide glass was allowed to stand to dry and then observed with an optical microscope. The Gram-positive bacteria are blue-violet, the Gram-negative bacteria are pink, and the lactic acid bacteria should show positive reaction.

(2) Preparation of Radix Polygalae Powder

Radix Polygalae is the root of the perennial herb *Polygala tenuifolia* willd. or *Polygala sibirica* L. 50 g of Radix Polygalae medicinal materials were weighed in laminar flow, poured into a high-speed sterilized and dried pulverizer for homogenization, sieved through a sterile 60-mesh stainless steel mesh sieve and stored at −30° C.

(3) Screening of Acid-Resistant Lactic Acid Bacteria

Preliminary screening: Three kinds of aging broths of fruit and vegetable fermentation juice obtained from the Taiwan Enzyme Village Co., Ltd. were diluted 10 folds successively with PBS, and applied to a MRS/NaN$_3$/cycloheximide agar plate, the pH value of which was adjusted with acetic acid to be pH 4.2, 4.8 and 5.2. After being anaerobically incubated at 37° C. for 7 to 9 days, the colonies were selected according to the appearance of the colony (such as size, shape, etc.). After being applied and purified by restreaking on the same agar plate twice, 19 isolates of acid resistance strains were obtained. The colonies of these isolates and non-acid-resistant lactic acid bacteria *Lactobacillus paracasei* (Lp) (lactic acid bacteria of the control group) were cultured in the MRS broth, and then inoculated at 10% in the pineapple or the papaya fermentation juice (5 mL) of the Taiwan Enzyme Village Co., Ltd., which had been fermented for at least 7 months, and added with 1% peptone and yeast extract (PY). After being cultured at 30° C. for 3 to 4 days, 15 isolate were able to grow in these two fermentation juice. Further, 12 isolates of positive bacteria were identified with the Gram staining method. These 12 isolates and Lp were inoculated again in the same manner in 40 mL of the pineapple or the papaya fermentation juice, then 4 isolates were obtained and their viable bacteria counts in these 2 re-fermentation juices were as high as $10^6$ CFU/mL. The present invention selected one of the isolates for subsequent experiments.

(4) Strain Identification

The identification of the scientific name of the selected isolate by the Food Industry Research and Development Institute of Taiwan showed that the isolate was a Gram-positive bacterium. The Gram-positive bacterium did not have the properties of a catalyst, an oxidase and motility, and it would grow in an anaerobic environment, but not in an aerobic one, and would not produce endospores. The 16S rDNA sequence of the isolate was SEQ ID NO: 1. According to the 16S rDNA sequence analysis and the physiological and biochemical test and analysis results (as shown in Table 1), its similarity to the acid-resistant lactic acid bacteria *Lactobacillus acetotolerans* was as high as 99.9%. Therefore, the isolate was named by the present invention as *L. acetotolerans* LE36 (LE36). LE 36 has been deposited under the Budapest Treaty at Leibniz Institute DSMZ-German Collection of Microorganisms and Cell Cultures (Inhoffenstr. 7B, D-38124 Braunschweig, Germany) on Jun. 24, 2019 and has been given the DSMZ Accession No. DSM 33168 by the International Depositary Authority. This biological material was subjected to the viability test and passed.

TABLE 1

Physiological and biochemical test results of LE36

|  | LE36 | *L. acetotolerans* BCRC 17709[1] |
|---|---|---|
| Glycerol | − | − |
| Erythritol | − | − |
| D-Arabinose | − | − |
| L-Arabinose | − | − |
| D-Ribose | − | − |
| D-Xylose | − | − |
| L-Xylose | − | − |
| D-Adonitol | − | − |
| β-Methyl-xylopyranoside | − | − |
| D-Galactose | − | − |
| D-Glucose | + | + |
| D-Fructose | + | / |
| D-Mannose | + | + |
| L-Sorbose | − | − |
| L-Rhamnose | − | − |
| Dulcitol | − | − |
| Inositol | − | − |
| D-Mannitol | − | + |
| D-Sorbitol | − | − |
| α-Methyl-D-mannopyranooside | − | − |
| α-Methyl-D-glucopyranoside | − | − |
| N-Acetyl-glucosamine | + | + |
| Amygdalin | − | − |
| Arbutin | − | − |
| Esculin | − | − |
| Salicin | − | − |
| D-Cellobiose | − | − |
| D-Maltose | − | − |
| D-Lactose | − | − |
| D-Melibiose | − | − |
| D-Saccharose | − | − |
| D-Trehalose | + | + |
| Inulin | − | − |
| D-Melezitose | − | − |
| D-Raffinose | − | − |
| Amidon | − | − |
| Glycogen | − | − |
| Xylitol | − | − |
| Gentiobiose | − | − |
| D-Turanose | − | − |
| D-Lyxose | − | − |
| D-Tagatose | − | − |
| D-Fucose | − | − |
| L-Fucose | − | − |
| D-Arabitol | − | − |
| L-Arabitol | − | − |
| Gluconate | − | − |
| 2-keto-Gluconate | − | − |
| 5-keto-Gluconate | − | − |

−: Negative reaction ; +: Positive reaction ; /: Between positive and negative reactions.
*L. acetotolerans* BCRC 17709$^T$ was *Lactobacillus acetotolerans* type strain.

(5) pH and Temperature Tolerance Test

The one-time activated bacterial culture of lactic acid bacteria *Lactobacillus rhamnosus* GG (LGG), *Lactobacillus acetotolerans* type strain (La) (purchased from the Food Industry Research and Development Institute) and LE36 were incubated for 24 hours. After the absorbance (OD600) of the bacterial culture were measured at 600 nm wavelength, the remaining bacterial culture were centrifuged at 3000 g for 10 minutes at room temperature, dissolved in an appropriate amount of MRS broth and adjusted to OD=1, inoculated with OD600=0.02 in MRS broth having a pH value of 5.4, 4.8 and 4.2, respectively, and cultured for 144 and 96 hours at 37° C. and 42° C., respectively. Samples were collected and OD600 was measured at the 0th, 12th, 18th, 24th, 48th, 72nd, 96th and 144th hours.

(6) Preparation of Re-Fermentation Juice (a) Re-fermentation and preparation of 5 kinds of vegetable and fruit fermentation juice: one-time activated bacterial culture was inoculated in 20 mL of MRS broth at 1%. After being cultured in an incubator at 37° C. for 18 hours, it was centrifuged at 3000 g, room temperature for 10 minutes and then resuspended in 5 mL of MRS broth, which was a 4-fold concentrated bacterial culture. 80 mL of the pineapple, papaya, bean sprouts, jaboticaba, and grapefruit/pumpkin/tangerine fermentation juice (abbreviated as AZ, PZ, BZ, JZ and FQSZ) were added with 1% PY and 2% Radix *Polygala* powder, and mixed well. An appropriate amount of samples (sample on day b) were collected. The remaining re-fermentation juice were inoculated with 4 folds concentrated bacterial culture of LGG, La, and LE36, respectively. After being well mixed, an appropriate amount of samples (samples on day 0) were collected. The remaining re-fermentation juice were cultured at 30° C., and an appropriate amount of samples were collected on day 2 and day 4 during the fermentation (samples on day 2 and 4, respectively).

(b) Re-fermentation and preparation of bean sprouts fermentation juice: the preparation method was similar to the re-fermentation and preparation of the above 5 kinds of vegetable and fruit fermentation juice; except that the bean sprouts fermentation juice was the only fermentation juice, the concentrated bacteria were prepared by inoculating 1% one-time activated bacterial culture in 50 mL of MRS broth, and then cultured in an incubator at 37° C. After being incubated for 36-40 hours, the bacterial culture was collected to measure the OD600. When it was greater than 1.2, the bacterial culture was collected and washed once with 50 mL of PBS. It was centrifuged at 3000 g for 10 minutes at room temperature and then resuspended in an appropriate amount of MRS broth. The concentrated bacterial culture was adjusted to OD600=10. 0.5 mL was collected for lactic acid bacteria plating and counting. Additional samples, which were fermented for 6 and 14 days, were collected. In addition, after samples were collected, a portion of the samples were centrifuged at 5000 g for 15 minutes, and the supernatants were collected. For those samples that were not centrifuged, after the pH was measured and the number of lactic acid bacteria was counted and analyzed on the day of the sampling, all re-fermentation juice and their supernatant samples were respectively packed and stored at −30° C.

(7) Measurement of Reducing Sugar

Serial dilutions of samples and standards were prepared with sterile water. 120 μL of sterile water (blank group), glucose standard dilution (standard group), and sample dilution (sample group) were placed in a 1.5 mL microcentrifuge tube, then 120 μL of 3,5-Dinitrosalicylic acid (DNS) reagent was added and thoroughly mixed, then treated in a dry bath at 95° C. for 5 minutes, cooled at room temperature for 10 minutes, vortexed for 10 seconds and then spun down. 200 μL was placed in a 96-well plate, and OD540 was measured. The results were obtained from the linear regression equation based on the concentration and absorbance of 0, 0.125, 0.25, 0.5, 1.0, 2.0, and 5.0 mg/mL of the glucose standard dilutions. The absorbance of the sample dilution was fitted into the linear regression equation to estimate the glucose equivalent (GE) of the reducing sugar of the stock solution.

(8) Measurement of Flavonoids

The yellow flavon-aluminum complex produced by the reaction of aluminum trichloride and flavonoid compounds was utilized to quantitatively determine the flavonoids content, because the yellow shade of the complex was proportional to the amount of flavonoids. Samples and standard dilutions were freshly prepared by using 40% ethanol. 50 μL of quercetin standard dilution (standard group) and sample dilution (sample group) were placed in a 96-well plate, then 100 μL of 0.4% sodium nitrite ($NaNO_2$) was added, shaken at 28° C. for 15 seconds, and allowed to stand for 5 minutes and 45 seconds. Subsequently, 10 μL of 12% aluminum trichloride was added, shaken at 28° C. for 15 seconds, allowed to stand for 4 minutes and 45 seconds, 40 μL of 1 M NaOH was added and shaken for 45 seconds, and then the OD510 was measured. The total content of the flavonoids in the sample was obtained from the linear regression equation based on the concentrations and absorbance of 10, 50, 100, and 200 mg/mL of quercetin standards. The absorbance of the sample dilution was fitted into the linear regression equation to estimate the quercetin equivalent (QE) of the flavonoids in the sample stock solution.

(9) Cultivation of RAW264.7 Cells (a) Freezing the cells: When the cells grew up to 80% of the total volume, the old culture medium was removed and discarded, and the cells were washed two times with PBS, 0.05% trypsin/EDTA was added to react for 3 minutes. An appropriate amount of the culture medium (2-3 mL) was added for neutralization with trypsin/EDTA, the suspended cells were obtained by pipetting, placed in a 15 mL centrifuge tube and centrifuged at 1200 rpm for 10 minutes to prepare a frozen cell solution containing 7% DMSO culture medium. After the cells were centrifuged, the supernatant was removed, and the prepared culture medium containing 7% DMSO was added to mix the cells thoroughly, 1000 μL of the cell suspension was collected and placed in a frozen centrifuge tube, placed in a gradually-freezing box and stood at −80° C. overnight, then moved to a liquid nitrogen tank for storage the next day.

(b) Thawing the cells: The frozen cells were taken out of the liquid nitrogen tank, first thawed in a water bath at 37° C., and the outside of the cryotube was wiped with 75% alcohol, and then transferred in laminar flow for operation. The cell culture was placed in a centrifuge tube containing 3 mL of fresh culture medium to neutralize DMSO, centrifuged at 1200 rpm for 10 minutes, the supernatant was discarded, and an appropriate amount of fresh culture medium, about 1 mL, was added, resuspended in a 10 cm culture dish containing 10 mL of fresh culture medium, incubated in a 5% carbon dioxide incubator at 37° C.

(c) Subculture of the cells: when the cells grew up to 80% of the total volume, the culture medium was removed and discarded, and the cells were washed with 5 mL of PBS two times, and then 1 mL of 0.05% trypsin-ETDA was added to suspend the cells. An appropriate amount (2-mL) of culture medium was added for neutralization with trypsin/EDTA, and the suspended cells were obtained by pipetting and then placed in a 15 mL centrifuge tube. After being centrifuged at 1200 rpm for 10 minutes, the supernatant was discarded and the cells were resuspended in 3 mL of fresh culture medium. An appropriate amount of cell culture was applied for cell count, and then reinoculated in a culture dish containing fresh culture medium.

(d) Cell count: a hemacytometer plate chamber was obtained, and 2 grooves next to the chamber and the surfaces of cover glasses were wiped with alcohol. The cover glasses were placed on 2 grooves. The cell suspension was diluted 5 to 25 folds with trypan blue solution and mixed thoroughly. 10 μL of stained cell solution was filled in each of the two grooves on the side of the hemocytometer plate chamber. Under a microscope, the number of cells in a large grid of each of four corners of the two chambers was counted by a counter. The original viable cell concentration (cells/mL) was calculated by using the following equation: total cell number of 8 large grids/8/$10^{-4}$ (the volume of 1 large grid; mL)×5 (cell dilution fold)×5 (trypan blue dilution fold).

Lipopolysaccharide (LPS) drug stimulation and treatment: in the analyses of NO production and cell viability, when the cells grew up to 80% of the total volume, after the above-described cell treatment and cell count, the cell number was adjusted with DMEM culture medium to $10^6$ cells/mL, and 200 μL of cell solution was seeded in a 96-well cell culture plate. After being placed in a cell culture incubator for cultivation for 24 hours, the supernatant was removed and discarded. 100 μL of phenol red free DMEM medium, 100 μL of L-NMMA (positive control group; final concentration 0.1 mM) or re-fermentation juice diluted with the same culture medium containing LPS (final concentration 0.1 μg/mL) was added, then placed in a cell incubator for cultivation and stimulation of the cells for 24 hours. The above was the drug treatment of the drug and LPS simultaneous treatment group. The supernatants of all cell culture were collected for NO production, and the cells adhered to the plate were used for cell viability analysis.

(10) Analysis of NO Production

100 μL of the RAW264.7 cells supernatant was collected and placed in a new 96-well cell culture plate. An equal volume of Griess reagent A and Griess reagent B mixture solution was added, and OD550 was measured after incubation for 15 minutes at room temperature in dark. Linear regression was then performed with 0, 20, 40, 60, 80, and 100 μM of sodium nitrite ($NaNO_2$) standards and the absorbance, so the absorbance of the sample dilution was fitted into the linear regression equation to calculate the NO content of the sample stock solution. The equation for calculating the relative inhibition rate of NO was: (NO production amount of the "−" group [negative control group; sample treatment without LPS group]−NO production amount of each sample with LPS)/(NO production amount of the "−" group)×100%.

(11) Cell Viability Analysis

The above-described RAW 264.7 cells treated and adhered to a 96-well plate were added to 200 μL of 0.05 mg/mL MTT, and placed in a cell culture incubator for reaction for 4 hours. At this time, the yellow and soluble MTT was reduced by the succinate dehydrogenase secreted from the survived cell mitochondria into an insoluble purple crystalline formazan so as to be precipitated. Then, the supernatant on the culture plate was removed and discarded, 200 μL of DMSO was added, and shaken in the dark for 10 minutes. After the purple crystals were completely dissolved, the OD570 was measured. Finally, the cell viability of the blank group with no added LPS and sample was set as 100%, and the cell viability of the experimental group was estimated.

(12) Statistical Analysis

The statistical data of the present invention were plotted by using a statistical software (GraphPad Prism 5) and presented as mean value±standard error of the mean (SEM). After the one-way ANOVA analysis, the Tukey's post-hoc test was performed and $p<0.05$ was considered as statistically different.

Experimental Result (1) Screening of Acid-Resistant Lactic Acid Bacteria 3 samples were collected from aging broths of fruits and vegetables in the Taiwan Enzyme Village Co., Ltd., after appropriate dilution, they were plated on MRS/cycloheximide/sodium azide ($NaN_3$) agar plates at pH 4.2, 4.8 and 5.2. 0, 38 and 10 colonies were respectively obtained, and colonies were selected according to the appearance of the colonies (such as size, shape, etc.) then purified two times by the same agar plates. 19 isolates and 1 isolate were selected respectively from the isolates at pH 4.8 and 5.2. The one-time activated bacterial culture of the former 19 isolates with acid-resistant potential, together with the non-acid-resistant lactic acid bacteria Lp (*L. paracasei*) control group, were respectively inoculated in the pineapple and papaya fermentation juice, which had been fermented for at least 7 months (pH values were 3.2 and 3.4, respectively) in Taiwan Enzyme Village Co., Ltd. 15 isolates capable of growing in these two fermentation juices were obtained, and another 4 isolates were able to survive only in the papaya fermentation juice. 12 isolates further identified from the former by using the Gram staining method were positive bacteria. These 12 isolates were re-inoculated in the above two fermentation juices, but the volume was expanded from 5 mL to 40 mL. Finally, 4 strains of isolates capable of growing in these two fermentation juices with a cell number exceeding $10^6$ CFU/mL were obtained. This experiment selected one of the isolates for strain identification and subsequent experiments. After the isolate was identified, the present invention renamed the isolate as LE36.

(2) Growth Curves of LE36 Cultured at Different Temperatures and pH Values

Since LE36 was capable of stably growing in the pineapple and papaya fermentation juice at pH 3.2 and pH 3.4, the present invention therefore further examined the amount of growing bacteria in the MRS broth at different pH values prepared by using acetic acid, and simultaneously examined their tolerance to high temperature (42° C.). At the same time, in order to compare whether the acid resistance property of LE36 was the general physiological property of the strain, the present invention simultaneously examined the *Lactobacillus acetotolerans* type strain (La) purchased from the Food Industry Research and Development Institute. In addition, *Lactobacillus rhamnosus* GG (LGG), which had an immune function but was not an acid-resistant lactic acid bacteria, was simultaneously examined. The results are shown in FIG. 1, under the standard culture temperature of 37° C. and the standard pH of 5.4, LE36 and LGG reached OD 1.5 after being cultured for 12 hours, and continued to increase slightly to OD 1.9 after 144 hours (FIG. 1A). When La was cultured under the same condition, OD 1.3 was merely maintained after 18 hours of cultivation, and OD 1.5 to 1.7 was barely maintained after 24 hours. Under the standard culture temperature of 37° C. and the acidity at pH 4.8, OD 1.5 was reached after LE 36 and LGG were cultured for 18 hours, and continued to increase slightly to OD 1.8 after 144 hours (FIG. 1C). As to La, it took 18 hours of cultivation to reach OD 1.2, and OD 1.5-1.6 was barely maintained after 48 hours. Under the standard culture temperature of 37° C. and strong acidity of pH 4.2, it took 18 hours of cultivation for LE36 to reach OD 0.8, increased to OD 1.5 after 36 hours, and then maintained at OD 1.6-1.7 (FIG. 1E). Under the same condition, it took 18 hours of cultivation for LGG to reach OD 0.5, and then continued to increase to OD 1.1 after 144 hours. As to La, only OD 0.7 was reached after 18 hours of cultivation, and slightly increased to OD 1.4 after 144 hours (FIG. 1E).

Under a high temperature of 42° C. and the standard pH of 5.4, LE36 and LGG reached OD 1.1 and 1.0, respectively, after 24 hours of cultivation, but La only reached OD 0.6 (FIG. 1B). However, after 36 hours, all three reached about OD 1.3, and slightly increased to OD 1.4-1.5 after 96 hours. Under a high temperature of 42° C. and an acidity of pH 4.8, LE36 and LGG reached OD 0.8 and 0.7, respectively, after 24 hours of cultivation, and reached OD 1.1 and OD 1.0 after 96 hours of cultivation (FIG. 1D). Under the same condition, La only reached OD 0.5 after 24 hours of cultivation, and OD 0.9 was reached after 96 hours. At a high temperature and strong acidity of pH 4.2, LE36, La and LGG did not exceed OD 0.6 during a 96 hour-cultivation period (FIG. 1F).

Experimental results showed that LE36 and LGG grew better than La at 37° C. and pH 5.4 and 4.8, and the growth condition of LE36 at pH 4.2 was better than the other two strains. Therefore, LE36 had a good acid resistance effect and was suitable for being inoculated to a vegetable and fruits fermentation juice with a pH of 3-4.

(3) Number of Viable Bacteria and Anti-Inflammatory Effect of LE36 Inoculated in Different Fermentation Juices Supplemented with Radix *Polygala*

LE36 bacterial culture was inoculated in 5 kinds of fermentation juice containing 2% Radix *Polygala* powder, including the pineapple, papaya, bean sprouts, jaboticaba, and grapefruit/pumpkin/tangerine fermentation juice, and after being incubated for 4 days, AZ, PZ, BZ, JZ and FQSZ re-fermentation juice were obtained. The pH values after fermentation were shown in FIG. 2A, and all of the re-fermentation juice maintained the original pH value (3.3-3.8). The number of vial lactic acid bacteria was shown in FIG. 2B, all of the re-fermentation juice were fermented for 2 and 4 days, the number was about the same as when they were inoculated ($1.2 \times 10^6$-$1.4 \times 10^8$ CFU/mL). It showed that LE36 was able to stably survive in these re-fermentation juices.

Figure 2:
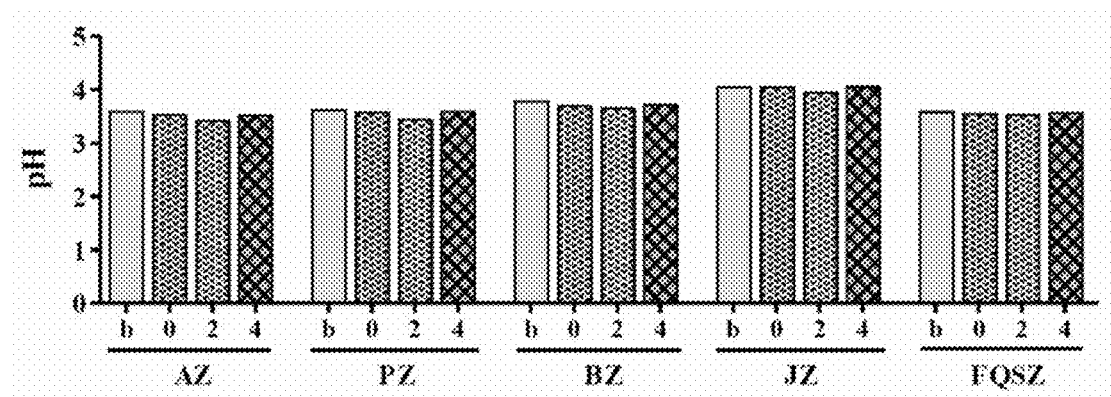
FIG. 2 shows the pH (FIG. 2A), the viable bacteria count (FIG. 2B) of different fermentation juices supplemented with Radix Polygalae in which the *Lactobacillus acetotolerans* LE36 is inoculated, and the relative cell viability (FIG. 2C) and the relative NO inhibition rate (FIG. 2D) of the fermentation juices co-treated with lipopolysaccharide (LPS) in RAW264.7 mouse macrophages. The two-time activated concentrated bacteria of *Lactobacillus acetotolerans* LE36 (LE36) is inoculated at 1% in a pineapple, papaya, bean sprouts, jabuticaba, and grapefruit/pumpkin/tangerine fermentation juice supplemented with Radix Polygalae, respectively, and then incubated at 30° C. for 4 days. Appropriate amount of all re-fermentation juice (the pineapple fermentation juice (AZ), the papaya fermentation juice (PZ), the bean sprouts fermentation juice (BZ), the jabuticaba fermentation juice (JZ) and the grapefruit/pumpkin/tangerine fermentation juice (FQSZ)) before (b) and after LE36 inoculation for 0, 2 and 4 days (0, 2, and 4) are respectively collected (FIGS. 2C and 2D). After RAW264.7 mouse macrophages (0.2 mL; $10^6$ cells/mL) are seeded for 24 hours, LPS (100 ng/mL; negative control group; "−" group) is added, and then co-treated with L-NMMA (1 mM; NO synthase inhibitor; positive control group; "+" group) or heat-treated (80° C., 20 minutes) re-fermentation juice (AZ, PZ, BZ, JZ and FQSZ are respectively 75-, 75-, 75-, 250- and 75-fold dilutions) for 24 hours, the cell viability and the NO production level are measured. The relative cell viability (FIG. 2C) is measured by using the MTT assay, in which the blank group without LPS stimulation and juice treatment is set as 100%. The NO production level is analyzed by using the Griess reagent method, and then the NO content of the original sample solution is obtained from a linear regression equation based on the standard concentration (0-100 M) and the absorbance of sodium nitrite ($NaNO_2$), and into which the absorbance of the sample dilution is fitted. The calculation of relative NO inhibition rate (FIG. 2D) is (NO production level of the "−" group−NO production level of each juice added with LPS)/(NO production level of the "−" group)×100%. The experimental data is the mean value±standard error of the mean (SEM) of three duplicates.
Figure 2:
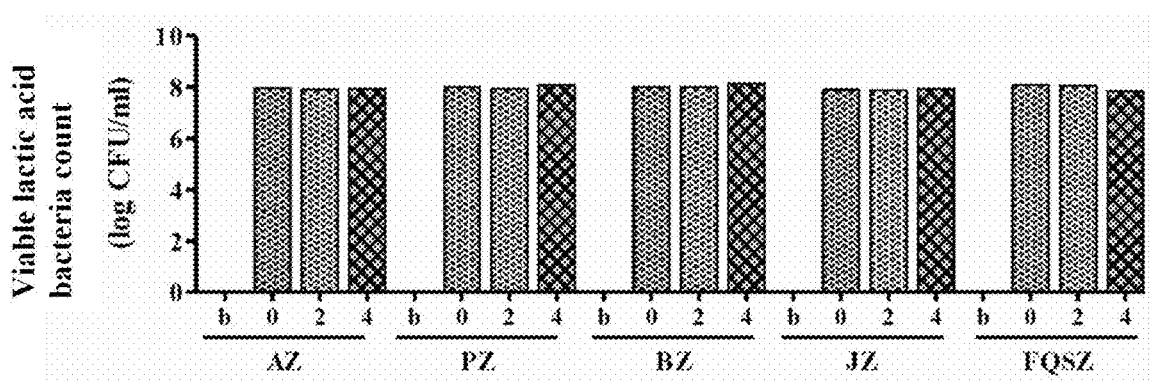
Figure 2:
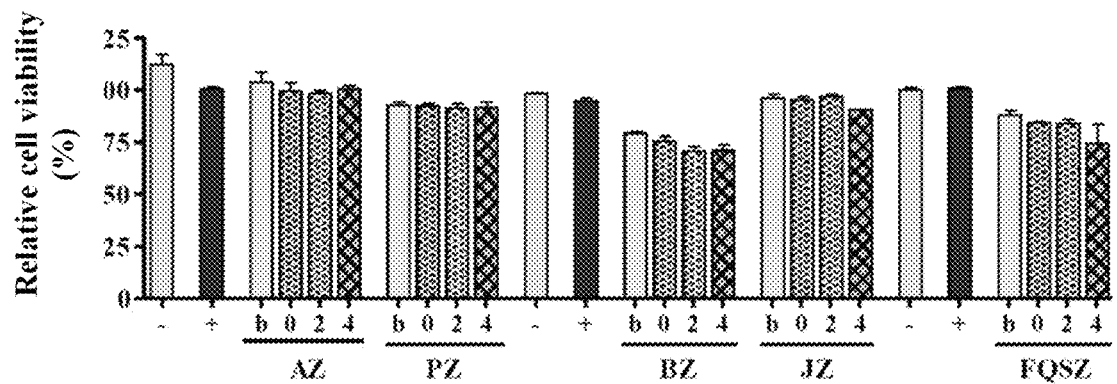
Figure 2:
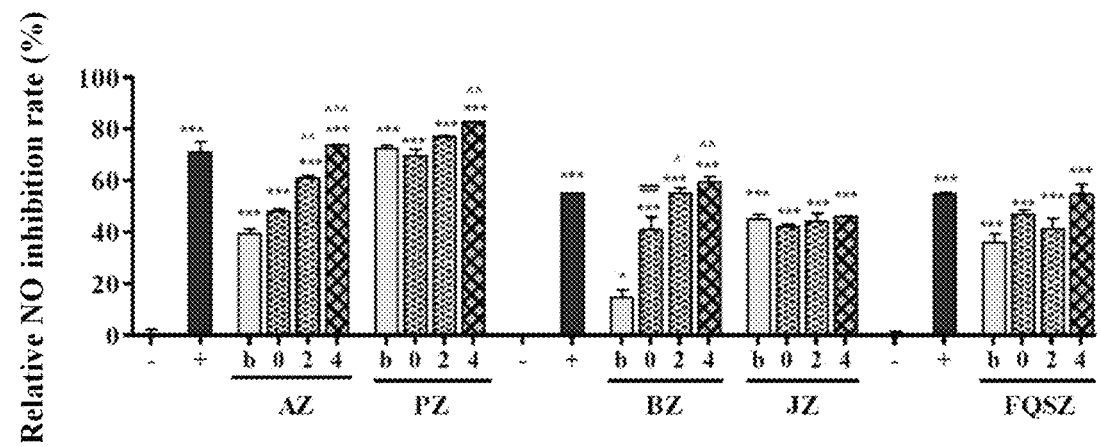

As to the anti-inflammatory aspect of the thermally treated supernatant samples of the re-fermentation juice in LPS-stimulated RAW264.7 cells, under the premise that the relative cell viability of all samples was higher than 70% (FIG. 2C), the relative NO inhibition rate of each sample was as shown in FIG. 2D. When the re-fermentation juice after being inoculate (day 0) was compared to before being inoculated (day b), only BZ had a significant increase of 181% (p<0.001). As compared to 0 day of fermentation, the NO inhibition rate of AZ, PZ and BZ increased significantly by 53%, 19% and 46%, respectively (p<0.001, p<0.01 and p<0.01). There was no significant difference between JZ and FQSZ re-fermentation juice after 2-4 days of fermentation.

It was found from the experimental results that when LE36 was added to the BZ fermentation juice, the anti-inflammatory effect was increased by 181%, indicating that the lactic acid bacterium itself had a significant anti-inflammatory ability. After 2 and 4 days of fermentation, the number of lactic acid bacteria continued to increase.

It was found from the experimental results that when LE36 was inoculated in five fermentation juice to be tested, it was able to stably survive in all of them. In a cell experiment, LE36 was added to the BZ fermentation juice, and the anti-inflammatory effect increased by 181%, indicating that the lactic acid bacterium itself had a significant anti-inflammatory ability. As the days of fermentation after inoculation increased, the effect of the AZ, PZ and BZ re-fermentation juice on the NO inhibition rate of the RAW264.7 cells also increased significantly, indicating that LE36 significantly improved the anti-inflammatory effect of these three fermentation juices.

Finally, combining the above experimental results, the present invention selected "bean sprouts" for further fermentation analysis.

(4) Viable Bacteria Count, Reducing Sugar Level, Antioxidation Analysis and Anti-Inflammatory Effect of LE36 Inoculated in Bean Sprouts Fermentation Juice and its Re-Fermentation Juice Supplemented with Radix *Polygala*

(a) Viable Bacteria Count

The bacterial culture of LE36 and the control group La and LGG were respectively inoculated in a bean sprout fermentation juice or a bean sprout fermentation juice supplemented with 2% Radix *Polygala*. After being incubated for 14 days, B and BZ re-fermentation juices were obtained. The pH values during the fermentation process were shown in FIG. 3A, and there was no noticeable changes and all pH values were maintained at pH 3.6.

As to the viable bacteria count of the re-fermentation juice B (FIG. 3B), when LE36 was inoculated for 14 days, the number of viable lactic acid bacteria was slightly increased from the original $6.6 \times 10^7$ CFU/mL to $1.6 \times 10^8$ CFU/mL. As to LGG, the number was reduced from the original $1.9 \times 10^7$ CFU/mL to 21 CFU/mL after 2 days of fermentation, and no viable bacteria was found after 4 days of fermentation. As to La, the number was reduced from the original $4.4 \times 10^6$ CFU/mL to $1.0 \times 10^5$ CFU/mL, 7.0 CFU/mL and 20 CFU/mL, respectively, after 2, 4, and 6 days of fermentation, and no viable bacterial was found after 14 days of fermentation.

As to the viable bacteria count in the re-fermentation juice BZ (FIG. 3B), 14 days of fermentation after inoculation of LE36, the viable bacteria count increased from the original $5.4 \times 10^7$ CFU/mL to $2.5 \times 10^8$ CFU/mL. As to the inoculated control group LGG, the viable bacteria count reduced from the original $2.5 \times 10^7$ CFU/mL to $1.4 \times 10^2$ CFU/mL, and no viable bacteria was found after 14 days of fermentation. As to La, the viable bacteria count reduced from the original $5.3 \times 10^6$ CFU/mL to $1.0 \times 10^3$ CFU/mL when the fermentation lasted for 14 day. It was found from the results of the fermentation, after 14 days of fermentation of the bean sprouts fermentation juice innoculated with the LE36, the isolate selected by the present invention, the viable bacteria count was not reduced, but continued to grow.

(b) Reducing Sugar Content

Figure 3:
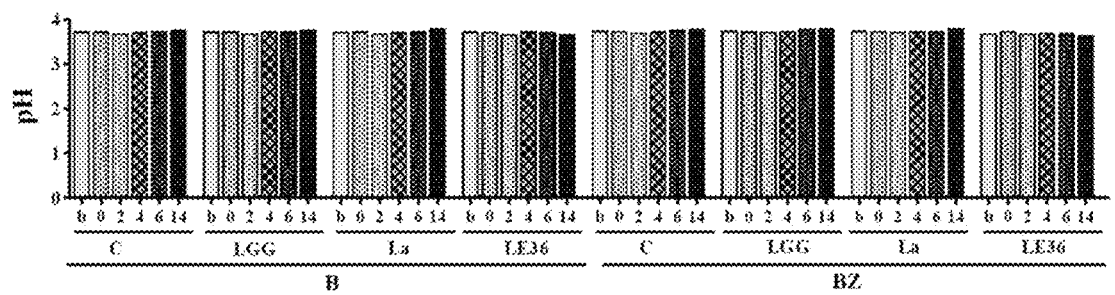
FIG. 3 shows the pH (FIG. 3A), the viable bacteria count (FIG. 3B), the reducing sugar content (FIG. 3C), and the flavonoids content (FIG. 3D) of the bean sprouts fermentation juice and its re-fermentation juice supplemented with Radix Polygalae in which the *Lactobacillus acetotolerans* LE36 is inoculated, and the relative cell viability (FIG. 3E) and the relative NO inhibition rate (FIG. 3F) of the above re-fermentation juice co-treated with LPS in RAW264.7 macrophages. The two-time activated concentrated bacteria of *Lactobacillus acetotolerans* LE36 (LE36), and the control groups *Lactobacillus acetotolerans* type strain (La) and *Lactobacillus rhamnosus* GG (LGG) at OD600=0.02 are inoculated in the bean sprouts fermentation juice supplemented with or without Radix *Polygala* powder and then incubated at 30° C. for 14 days. Appropriate amount of the resulted re-fermentation juice (B and BZ) before (b) and after inoculation for 0, 2, 4, 6 and 14 days (0, 2, 4, 6 and 14) are collected. The reducing sugar content (FIG. 3C) and the flavonoids content (FIG. 3D) are respectively measured by using dinitrosalicylic acid and aluminium chloride, and then the glucose equivalent (GE) of the reducing sugar and the quercetin equivalent (QE) of the flavonoids of the original sample solutions are respectively estimated from the linear regression equation based on the concentration and absorbance of the standard glucose (0.125-2 mg/mL) and the quercetin standard concentration (10-200 μg/mL), and into which the absorbance of the sample dilution is fitted. The experimental results of the relative cell viability (FIG. 3E) and the relative NO inhibition rate (FIG. 3F) of the heat-treated (80° C., 20 minutes) re-fermentation juice (B and BZ are 25- and 50-fold dilution, respectively) are as shown in FIG. 3.
Figure 3:
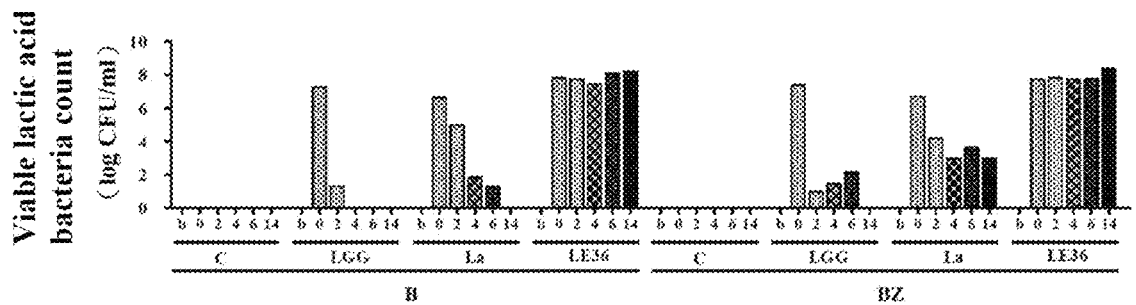
Figure 3:
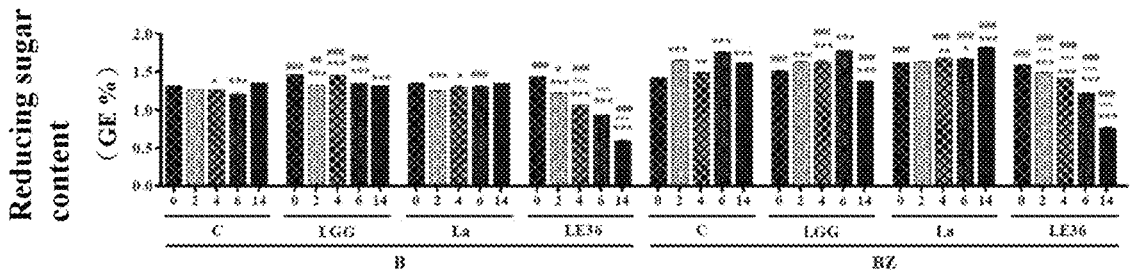

The reducing sugar content of the LE36-inoculated re-fermentation juice B was as shown in FIG. 3C, when 2, 4, 6 and 14 days of fermentation were compared to 0 day of fermentation, the content was significantly decreased by 3%, 18%, 29% and 56%, respectively. As to the LE36-inoculated re-fermentation juice BZ, the content decreased significantly by 11%, 15%, 33% and 52%, respectively. As to other re-fermentation juices B and BZ inoculated with LGG and La, there was no significant difference in the reducing sugar content. It indicated that only LE36 had the fermentation effect of viable bacteria and consumed reducing sugar in two kinds of re-fermentation juice.

(c) Flavonoids Content

As to the flavonoids content (FIG. 3D), only the flavonoids content of the re-fermentation juice B inoculated with LE36 and fermented for 6 days significantly increased by 51.6%, as compared to that of day 0. There was no significant difference in the rest of the fermentation juice during the fermentation process.

(d) Anti-Inflammatory Activity

As to the anti-inflammatory effect on the LPS-stimulated RAW264.7 cells, the relative cell viability of all samples were higher than 60% (FIG. 3E). As to the relative NO inhibition rate (FIG. 3F), all re-fermentation juice had significant NO inhibition effects. The activity of the re-fermentation juice B inoculated with LGG, La, and LE36 increased slightly by 16%, 10%, and 13% after 0 day of fermentation, respectively, as compared to the un-inoculated blank group ($p<0.001$, $p<0.01$, and $p<0.001$), indicating that the bacteria themselves had the NO inhibition ability. After 14 days of fermentation, there was a significant increase of 50%, 60%, and 100%, respectively ($p<0.001$). As compared to the ones inoculated with La, LE36 significantly increased more by 30% ($p<0.001$).

The relative NO inhibition rate of the re-fermentation juice BZ was as shown in FIG. 3F, and all the re-fermentation juice had significant NO inhibition effects. The re-fermentation juice BZ inoculated with LGG, La and LE36 slightly increased by 14%, 32% and 34% after 0 day of fermentation, respectively ($p<0.05$, $p<0.001$ and $p<0.001$), as compared to the un-inoculated blank group; after 14 days of fermentation, there was a significant increase of 14%, 28%, and 56%, respectively ($p<0.01$, $p<0.001$, and $p<0.001$). As compared to La, LE36 significantly increased by 22% ($p<0.001$). Therefore, those inoculated with LE36 and fermented for 14 days had better NO inhibition activity. Therefore, regardless of the addition of Radix *Polygala* or not, all those inoculated with LE36 and fermented for 14 days had better anti-inflammatory effect on the NO inhibition activity.

Those skilled in the art recognize the foregoing outline as a description of the method for communicating hosted application information. The skilled artisan will recognize that these are illustrative only and that many equivalents are possible.

What is claimed is:

1. A food composition, which comprises an acid-resistant lactic acid bacteria strain and an acidic fermentation juice, wherein the acid-resistant lactic acid bacteria strain is a *Lactobacillus acetotolerans* LE36 deposited under DSMZ Accession No. DSM 33168, wherein the said *Lactobacillus acetotolerans* LE36 is capable of stably growing in the fermentation juice at about pH 3.6, and wherein the acidic fermentation juice is bean sprouts fermentation juice.

2. The food composition of claim 1, wherein the food composition further comprises a Chinese herbal medicine or an extract thereof.

3. The composition of claim 1, wherein the *Lactobacillus acetotolerans* LE36 has a function of facilitating flavonoid production.

4. The composition of claim 1, wherein the *Lactobacillus acidophilus* LE36 has an anti-inflammatory function.

* * * * *

UNITED STATES PATENT AND TRADEMARK OFFICE
CERTIFICATE OF CORRECTION

PATENT NO. : 11,197,900 B2
APPLICATION NO. : 16/402253
DATED : December 14, 2021
INVENTOR(S) : Chia-Li Wei et al.

It is certified that error appears in the above-identified patent and that said Letters Patent is hereby corrected as shown below:

On the Title Page

Item (73) NATIONAL CHIAYI UNIVERSITY, Chiayi (TW) should be added after TAIWAN ENZYME VILLAGE CO. LTD., Chiayi (TW) as the second assignee.

Signed and Sealed this
Eleventh Day of April, 2023

Katherine Kelly Vidal
*Director of the United States Patent and Trademark Office*